United States Patent [19]
Forestier et al.

[11] Patent Number: 6,001,342
[45] Date of Patent: Dec. 14, 1999

[54] DEODORANT COMPOSITION AND USE THEREOF

[75] Inventors: Serge Forestier, Claye Souilly; Isabelle Rollat-Corvol, Boulogne, both of France

[73] Assignee: L'Oreal, Paris, France

[21] Appl. No.: 09/023,855

[22] Filed: Feb. 13, 1998

[30] Foreign Application Priority Data

Feb. 14, 1997 [FR] France .................................. 97 01750

[51] Int. Cl.$^6$ .................................................. A61K 25/00
[52] U.S. Cl. .......................................... 424/76.1; 424/401
[58] Field of Search ..................................... 424/76.1, 401

[56] References Cited

U.S. PATENT DOCUMENTS

| | | | |
|---|---|---|---|
| 4,708,821 | 11/1987 | Shimokawa et al. | 512/12 |
| 5,795,581 | 8/1998 | Segalman et al. | 424/400 |

FOREIGN PATENT DOCUMENTS

| | | |
|---|---|---|
| 0684044 | 11/1995 | European Pat. Off. . |
| 2368509 | 5/1978 | France . |
| WO 8201993 | 6/1982 | WIPO . |
| WO 9614346 | 5/1996 | WIPO . |
| WO 9630002 | 10/1996 | WIPO . |

OTHER PUBLICATIONS

Derwent Abstract of FR 2368509.

*Primary Examiner*—S. Mark Clardy
*Assistant Examiner*—Kathryne E. Shelbourne
*Attorney, Agent, or Firm*—Finnegan, Henderson, Farabow, Garrett & Dunner, L.L.P.

[57] ABSTRACT

A deodorant composition comprising at least one polymer selected from dendrimers containing terminal groups bearing a primary amine function, the use of these deodorant compositions for human topical application, and the use of selected dendrimers as deodorant active agents.

16 Claims, No Drawings

DEODORANT COMPOSITION AND USE THEREOF

The present invention relates to a deodorant composition, preferably a cosmetic composition, comprising at least one polymer selected from dendrimers containing terminal groups bearing a primary amine function, to the use of these compositions for human topical application and to the use of a polymer, selected from the dendrimers, as a deodorant active agent.

The invention also relates to a deodorization process using the deodorant composition and more especially a process for treating human underarm odors that involves applying an effective amount of the composition to the underarm area.

In the cosmetic field, it is well known to use deodorant products containing active substances such as antiperspirants or bactericides in topical application in order to reduce, or even eliminate, generally unpleasant underarm odors.

Antiperspirant substances have the effect of limiting the flow of sweat. They generally include aluminium salts which, on the one hand, are an irritant to the skin, and which, on the other hand, reduce the flow of sweat by modifying the skin physiology, which is unsatisfactory.

Bactericidal substances inhibit the growth of the skin flora responsible for underarm odors. Among the bactericidal products, the one most commonly used is Triclosan (5-chloro-2-(2,4-dichlorophenoxy)phenol), which has the drawbacks of considerably modifying the ecology of the skin flora and of being inhibited by certain compounds such as, for example, nonionic surfactants, which are commonly used in the formulation of cosmetic compositions. The insoluble nature of Triclosan in water does not allow its incorporation into essentially aqueous formulae.

With the aim of obtaining long-term efficacy, the search continues for novel products which exert the action of a deodorant active agent, i.e. products capable of modifying, of reducing, and/or of eliminating or preventing the development of body odor (this definition is given in the book "Cosmetic Science and Technology Series"—1988/Volume 7 chap. 10—IIIc). In addition, products are sought which do not have the drawbacks of the active substances used in the prior art.

It is known that certain basic compounds have the property of absorbing odors. Such is the case, for example, of sodium bicarbonate and zinc glycinate for which it is believed that the action comprises neutralizing the short-chain fatty acids responsible, among other compounds, for the unpleasant underarm odors.

It is known that certain polyamine compounds make it possible to limit the development of unpleasant odors. This is the case, for example, of polyethyleneimine (hyperbranched polymer), for which reference may be made to PCT patent application WO 82/01993. However, the efficacy of the known polyamine molecules is very insufficient and, in particular, it is observed that they have virtually no action only a few hours after having been applied.

After considerable research conducted in this direction, the inventors have discovered, surprisingly, that dendrimers containing terminal groups bearing a primary amine function have the property of preventing the development of unpleasant odors, without the drawbacks of the active substances previously employed in deodorant compositions, and with the advantage of being water-soluble in appreciable proportions sufficient to be readily formulated, especially in water-based cosmetic compositions for human topical application. These composition are also non-toxic and non-irritant.

A first subject of the present invention is thus a novel deodorant composition comprising at least one polymer selected from dendrimers containing terminal groups bearing a primary amine function.

A subject of the invention is also the use of the compositions more especially as, or for the manufacture of, cosmetic products intended for human topical application.

A subject of the invention is also the use of at least one polymer selected from dendrimers containing terminal groups bearing a primary amine function, as a deodorant active agent, in particular as an agent for inhibiting the development of odors.

Lastly, a subject of the invention is a deodorization process using the composition, and more particularly a process for treating human underarm odors, which involves applying an effective amount of the inventive composition to the underarm area.

Hyperbranched polymers, a category of polymer to which polyethyleneimine belongs, are molecular constructions having a branched structure, generally about a core. Their structure generally lacks symmetry because the monomer or base units involved in the construction of the hyperbranched polymer can be of varied nature and they are distributed non-uniformly. The branches in the polymer can also be of varied nature and length. The number of base units, or monomers, can also be different depending on the different branching.

Hyperbranched polymers are generally obtained from the polycondensation of one or more monomers ABx, A and B being reactive groups capable of reacting together, x being an integer greater than or equal to 2, but other preparation processes can be envisaged. Hyperbranched polymers are characterized by their degree of polymerization DP=1−b, b being the fraction of non-terminal functional groups in B which have not reacted with a group A. Since the condensation is non-systematic, in contrast with the synthesis of dendrimers, the degree of polymerization is less than 100%. Usually, by the known synthetic methods, their DP ranges from 15 to 90%.

Dendrimers are highly branched polymers and oligomers that are also known per se, having a well-defined chemical structure and are said to be "perfect" hyperbranched polymers. As a general rule, dendrimers comprise a core, a determined number of generations of branches, or spindles, and terminal groups. The generations of spindles contain structural units which are identical for the same generation of spindles and which can be identical or different for different generations of spindles. The generations of spindles extend radially in a geometrical progression from the core. The terminal groups of a dendrimer of the $N^{th}$ generation are the terminal functional groups of spindles of the $N^{th}$ generation or terminal generation. Such polymers are described in particular in D. A. Tomalia, A. M. Naylor and W. A. Goddard III, *Angewandte Chemie*, Int. Ed. Engl. 29, 138–175 (1990); C. J. Hawker and J. M. J. Frechet, *J. Am. Chem. Soc.*, 112, 7638 (1990); B. I. Voit, Acta Polymer, 46, 87–99 (1995); N. Ardoin and D. Astruc. Bull. Soc. Chim. Fr. 132, 875–909 (1995); G. R. Newkome, C. N. Moorefield, F. Vögtle, Dendritic Molecules, VCH Verlagsgesell-schaft, 1996, the disclosures of each of which are specifically incorporated by reference herein.

Dendrimers can also, more particularly, be defined by the formula (D1):

$$C[A_1B_1(A_2B_2(\ldots(A_{n-1}B_{n-1}(T)r_{n-1})r_{n-2}\ldots)r_2)r_1]s \qquad (D1)$$

in which:

C represents the core, linked by a number s of functional groups to s spindles $A_1B_1$ via the groups $A_1$;

s is an integer greater than or equal to 1 and less than or equal to the number of functional groups in C;

for each spindle $(A_1B_1)$ (i=1, 2 . . . n), the group $B_i$ is linked to $r_i$ groups $A_{i+1}$ of a spindle $(A_{i+1}B_{i+1})$;

each group $A_i$ (i≧2) is linked to a single group $B_{i-1}$ of the spindle $(A_{i-1}B_{i-1})$;

$r_i$ (i=1, 2 . . . n−1) represents the number of functional groups in the group $B_i$ belonging to the spindle $(A_iB_i)$, ri being an integer greater than or equal to 2;

the index i (i=1, 2 . . . n) is an integer which denotes the generation of each spindle;

the spindle of $n^{th}$ generation $A_nB_n$ is linked chemically to a number $r_n$ of terminal groups T, $R_n$ being an integer greater than or equal to zero.

The dendrimer definition given above includes molecules containing symmetrical branching; it also includes molecules containing non-symmetrical branching such as, for example, dendrimers whose spindles are lysine groups, in which the branching of one generation of spindles onto the preceding generation takes place on the amines α and ε of lysine, which leads to a difference in the length of the spindles for the different branching.

Dense star polymers, starburst polymers and rod-shaped dendrimers are included in the present definition of dendrimers. The molecules known as arborols and cascade molecules also fall within the definition of dendrimers according to the present invention.

Several dendrimers can be combined together, via a covalent bond or another type of bond, via their terminal groups in order to give species known as "bridged dendrimers" or "dendrimer aggregates". Such species are included in the definition of dendrimers according to the present invention.

Dendrimers can be in the form of a set of molecules of the same generation, these being so-called monodispersed sets; they can also be in the form of sets of different generations, which are known as polydispersed sets. The definition of dendrimers according to the present invention includes monodispersed sets, as well as polydispersed sets of dendrimers.

The invention relates more particularly to dendrimers containing terminal groups bearing a primary amine function.

Reference may be made to the following documents which describe dendrimers in which the terminal group contains an amine function, the content of these documents being specifically incorporated into the present description by reference: U.S. Pat. No. 4,694,064; U.S. Pat. No. 4,507,466; U.S. Pat. No. 4,631,337; U.S. Pat. No. 4,558,120; U.S. Pat. No. 4,568,737; U.S. Pat. No. 4,587,329; WO-A-9502008; WO-A-9314147; European Patent No. 234408; U.S. Pat. No. 4,289,872; U.S. Pat. No. 4,360,646; Proc. Natl. Acad. Sci. USA, 85, 5409–5413 (1988); WO 95/02008; and WO 93/14147.

The dendrimers containing terminal groups bearing a primary amine function are polyamidoamines such as, for example, those sold under the trade name STARBURST PAMAM by the company Dendritech (block copolymers of ethylenediamine and of methyl acrylate). They can also be selected from polyalkylamine-type dendrimers such as, for example, the polyethyleneimines and polypropyleneimines manufactured by the company DSM.

The dendrimers containing terminal groups bearing a primary amine function can also comprise a core and generations of base units, monomers or spindles, of any nature, on which a terminal group T bearing an amine function has been grafted.

When the dendrimer used is a polyamidoamine, it is preferably selected from those of generation 1, generation 2, generation 3, generation 4 and generation 5; more particularly from generation 1.

Preferably, the amine functions in the dendrimer are neutralized. This neutralization can give these molecules both better tolerance by the skin (keeping to physiological pH) and better efficacy for inhibiting the development of odors.

In the deodorant compositions according to the present invention, the dendrimer containing terminal groups bearing a primary amine function is generally present in weight proportions, calculated on a weight basis relative to the total weight of the composition, preferably ranging from approximately 0.01 to approximately 10%, more preferably ranging from approximately 0.1 to approximately 5%, and even more preferably ranging from approximately 0.1 to approximately 2%.

The deodorant compositions of the present invention can also comprise other standard deodorant active agents in addition to the dendrimers defined according to the invention.

These deodorant active agents can be selected, for example, from: water-soluble zinc salts such as, for example, zinc pyrrolidonecarboxylate (more commonly known as zinc pidolate), zinc sulphate, zinc chloride, zinc lactate, zinc gluconate and zinc phenolsulphonate; aluminium salts such as, for example, aluminium chloride and aluminium hydroxyhalides; zirconium salts such as, for example, zirconium oxide salts and hydroxyzirconyl salts; metal complexes such as aluminium or zirconium with an amino acid such as, for example, glycine, as described in U.S. Pat. No. 3,792,068, the disclosure of which is specifically incorporated by reference herein; and bactericides.

The deodorant compositions of the present invention are conventionally formulated according to the applications to which they are intended.

When the compositions are intended for cosmetic use, they are more particularly formulated in a cosmetically acceptable vehicle which can be, in particular, essentially aqueous, and contain $C_1$–$C_4$ monoalcohols, preferably ethanol, in order to accelerate evaporation of the product. The monoalcohols are generally present in amounts ranging from 15 to 50%, more preferably from 20 to 45%, and even more preferably from 25 to 35%.

The compositions according to the invention can also be formulated as a water-in-oil or oil-in-water emulsion or as a water-in-oil-in-water triple emulsion (such triple emulsions are known and described, for example, by C. Fox in "Cosmetics and Toiletries"—November 1986—Vol. 101—pages 101–112, the disclosure of which is specifically incorporated by reference herein), in which case the dendrimer is present in the aqueous phase of the emulsion.

The compositions of the invention can also comprise cosmetic adjuvants selected from fatty substances, organic solvents, gelling agents, emollients, softeners, antioxidants, opacifiers, stabilizers, silicones, anti-foaming agents, moisturizers, vitamins, fragrances, preserving agents, surfactants, fillers, sequestering agents, polymers, propellants, basifying or acidifying agents, dyes, pigments, thickeners or any other ingredient usually used in cosmetics.

surfactants are preferably selected from nonionic surfactants such as, for example, the condensation products of a fatty alcohol or of a fatty acid with a polyalkylene glycol chain.

The fatty substances can comprise an oil or a wax or a mixture thereof, petroleum jelly, paraffin, lanoline, hydrogenated lanoline, acetylated lanolin; they also comprise fatty acids, fatty alcohols such as lauryl, cetyl, myristyl, stearyl, palmityl or oleyl alcohol, as well as 2-octyldodecanol; fatty acid esters such as glyceryl monostearate, polyethylene glycol monostearate, isopropyl myristate, isopropyl adipate, isopropyl palmitate, octyl palmitate, $C_{12}$–$C_{15}$ fatty alkyl benzoates (FINSOLV TN from Finetex), myristyl alcohol polyoxypropylenated with 3 mol of propylene oxide (WITCONOL APM from Witco), or triglycerides of $C_6$–$C_{18}$ fatty acids such as caprylic/capric acid triglycerides.

The oils are selected from animal, plant, mineral or synthetic oils and, in particular, hydrogenated palm oil, hydrogenated castor oil, liquid petroleum jelly, liquid paraffin, purcellin oil (stearyl octanoate), silicone oils and isoparaffins.

The waxes are selected from animal, fossil, plant, mineral or synthetic waxes. Mention may be made in particular of beeswax, carnauba wax, candelilla wax, sugarcane wax, Japan wax, ozokerites, montan wax, microcrystalline waxes, paraffins and silicone waxes and resins.

The thickeners, preferably nonionic thickeners, can be selected from modified or unmodified celluloses and guar gums such as hydroxypropylated guar gum, cetylhydroxyethylcellulose, silicas such as, for example, BENTONE GEL MIO sold by the company NL Industries, or VEEGUM ULTRA sold by the company Polyplastic.

The compositions of the invention can also comprise emollients, which contribute towards a soft, dry, non-sticky feel when the composition is applied to the skin. These emollients can be selected from products such as volatile silicone, non-volatile silicones and other non-volatile emollients. Generally, the emollients are present in proportions ranging from 20 to 80%, more preferably from 25 to 60%, and even more preferably from 35 to 55%.

Volatile silicones are defined, in a known manner, as compounds that are volatile at room temperature. Among these compounds, mention may be made of cyclic and linear volatile silicones of the dimethylsiloxane type in which the chains comprise from 3 to 9 silicone residues. Preferably, cyclomethicones D4 or D5 are selected.

Non-volatile silicones are defined, in a known manner, as compounds with a low vapour pressure at room temperature. The following are included among these compounds: polyalkylsiloxanes, in particular linear polyalkylsiloxanes such as, for example, the linear polydimethylsiloxanes, or dimethicones, sold by the company Dow Corning under the name "DOW CORNING 200 FLUID"; polyalkylarylsiloxanes such as, for example, the polymethylphenylsiloxanes sold by the company Dow Corning under the name "DOW CORNING 556 FLUID"; polyether and siloxane copolymers such as, for example, dimethicone copolyols.

Among the non-volatile emollients which can be used in the present invention, mention may be made, for example, of: hydrocarbon derivatives, mineral oils, fatty alcohols, esters of $C_3$–$C_{18}$ alcohols with $C_3$–$C_{18}$ acids, esters of benzoic acid with $C_{12}$–$C_{18}$ alcohols and mixtures thereof, $C_2$–$C_6$ polyols preferably selected from glycerol, propylene glycol and sorbitol, and polyalkylene glycol polymers.

When the deodorant compositions according to the invention are intended for cosmetic use, they can be in the form of fluid gels, creams or lotions distributed as an aerosol spray, in a pump-dispenser bottle or as a roll-on, in the form of thick creams distributed in tubes and in the form of sticks, and, in this respect, they can contain the ingredients and propellants generally used in products of this type that are well known to those skilled in the art, provided that they do not interfere with the dendrimers described in the present invention.

The invention can also find advantageous applications in the field of various deodorizers and maintenance products, such as ambient air, textiles, refrigerators, waste chutes, dustbins, litters and cages for domestic animals or ventilation ducts in buildings.

Concrete, but in no way limiting, examples illustrating the invention will now be given.

EXAMPLE 1

Test 1

A test of inhibition of the development of odors was carried out on natural sweat.

Thus, the underarm sweat from several individuals was collected in a sauna and combined to make a sweat sample. 1 ml of the incubated sweat sample was introduced into each flask of active substance to be tested as well as into a control flask (without active substance). The active substance: x mg (x=1, 10, 20) of dendrimer selected from STARBURST PAMAM DENDRIMER of generation 1, 2, 3 and 5 (denoted PAMAM Gen 1 to 5) sold by the company Dendritech, was then introduced into each of the flasks of active substance to be tested respectively.

The flasks were then incubated at a temperature of 37° C. 4 to 6 evaluators then "sniff-tested" each of these flasks several times, with intervals of a few hours, and noted the intensity of the odor on a scale from 0 to 4.

Grade 0=no odor.

Grade 4=strong odor.

Results:

The results of these tests are given in Table 1:

TABLE 1

| Test | Active agent | Amount of active agent (mg of active agent per ml of sweat) | Grade of odor at t = 0 h | Grade of odor at t = 20 h | Grade of odor at t = 24 h |
|---|---|---|---|---|---|
| 1.1 | PAMAM Gen 1 | 1.8 | 0.3 | 0.3 | 0.7 |
|  |  | 17.9 | 0.4 | 0.2 | 0.5 |
|  |  | 35.9 | 1 | 0.5 | 0.3 |
| 1.2 | PAMAM Gen 2 | 2 | 0.2 | 1.6 | 2.5 |
|  |  | 20 | 0.7 | 0.4 | 0.5 |
|  |  | 40 | 0.7 | 0.5 | 0 |
| 1.3 | PAMAM Gen 3 | 2.1 | 0.3 | 0.6 | 2.7 |
|  |  | 20.9 | 0.1 | 1.7 | 2.5 |
|  |  | 41.7 | 0.9 | 0.4 | 2.3 |
| 1.4 | PAMAM Gen 5 | 2.3 | 0.4 | 1.3 | 2.5 |
|  |  | 22.7 | 0.3 | 2 | 2.3 |
|  |  | 45.4 | 0.7 | 0.5 | 2 |
| 1.5 | — | 0 | 0.1 | 2.5 | 2.7 |

These results show that the dendrimers have a large capacity for inhibiting the development of the odors in natural sweat for at least 20 hours and up to at least 24 hours for the dendrimers of the 1st and 2nd generations.

Test 2

The capacity of the dendrimers to prevent the development of odors was compared with that of other bases. The same procedure as in Example 1 was followed, using the following deodorant active agents:

a dendrimer, STARBURST PAMAM DENDRIMER of generation 1 at a content of 1 mg per ml of sweat, which gave a pH of 8.9 for the solution to be tested;

polylysine, sold by the company Chisso under the name POLYLYSINE, incorporated into the sweat in a sufficient amount to have a pH equal to 8.9;

sodium hydroxide, incorporated into the sweat in an amount sufficient to have a pH equal to 8.9.

The results of this test are given in Table 2:

TABLE 2

| Test | Active agent | Initial pH | Grade of odor at t = 0 h | Grade of odor at t = 20 h | Grade of odor at t = 24 h |
|---|---|---|---|---|---|
| 2.1 | PAMAM Gen 1 | 8.9 | 0 | 0.8 | 1.8 |
| 2.2 | POLYLYSINE | 8.9 | 0 | 2.6 | 2.8 |
| 2.3 | NaOH | 8.9 | 0 | 3.6 | 2.8 |
| 2.4 | — | 7.8 | 0 | 3.1 | 3.1 |

These tests show the superiority of the dendrimers over the known amines of the prior art, in particular over a linear polyamine polymer such as polylysine.

Test 3

The capacity of dendrimers to inhibit the development of odors was compared with that of other bases. The same procedure as in Example 1 was followed, using the following deodorant active agents:

a dendrimer, STARBURST PAMAM DENDRIMER of generation 1 at a content of 1mg per ml of sweat, which gave a pH of 8.8 for the solution to be tested;

polyethyleneimine (hyperbranched polymer) sold by the company BASF under the name POLYMIN G-35, incorporated into the sweat in a sufficient amount to have a pH equal to 8.8;

The results of these tests are given in Table 3:

TABLE 3

| Test | Active agent | Initial pH | Grade of odor at t = 14 h | Grade of odor at t = 20 h | Grade of odor at t = 24 h |
|---|---|---|---|---|---|
| 3.1 | PAMAM Gen 1 | 8.8 | 0.1 | 0.8 | 0.3 |
| 3.2 | Poyethyleneimine | 8.8 | 0.7 | 1.7 | 0.7 |
| 3.3 | — | 8.2 | 1.9 | 1.8 | 2.3 |

Test 4

In order to come closer to the conditions of a formulation which keeps to the physiological pH of the skin, a test of efficacy of the active agents was carried out at pH 7.

The same procedure as described above in Test 1 was thus carried out on two separate individuals with a single evaluation at 20 h, using sweat +active agent solutions neutralized with HCl in order to obtain a pH equal to 7. The following were thus tested:

4.1 - a dendrimer, STARBURST PAMAM DENDRIMER of generation 1, at a content of 1 mg per ml of sweat, which gave a pH of 8.9 for the solution to be tested;

4.2 - the solution 4.1 neutralized with HCl;

4.3 - a dendrimer, STARBURST PAMAM DENDRIMER of generation 5, at a content of 1 mg per ml of sweat, which gave a pH of 8.9 for the solution to be tested;

4.4 - the solution 4.3 neutralized with HCl;

4.5 - the control solution: no active agent, no neutralization.

The results of these tests are given in Table 4:

TABLE 4

| Test | Active agent | Initial pH | Grade of odor | Grade of odor |
|---|---|---|---|---|
| 4.1 | PAMAM Gen 1 | 8.8 | 0.8 | 1 |
| 4.2 | PAMAM Gen 1 | 7 | 0.3 | 0.5 |
| 4.3 | PAMAM Gen 5 | 8.8 | 1 | 1.3 |
| 4.4 | PAMAM Gen 5 | 7 | 0.5 | 0.3 |
| 4.5 | — | 8.2 | 2.1 | 2.6 |

These results show the superiority of neutralized dendrimers over non-neutralized dendrimers.

EXAMPLE 2

The following four formulae (two aqueous lotions, an aqueous stick and an oil-in-water emulsion) were prepared:

1 - Aqueous lotion:

| | |
|---|---|
| STARBURST PAMAM DENDRIMER of generation 1 | 0.5% |
| Fragrance | qs |
| Demineralized water | qs 100 |

2 - Aqueous lotion:

| | |
|---|---|
| STARBURST PAMAM DENDRIMER of generation 1 | 0.5% |
| Fragrance | qs |
| Preserving agent | qs |
| Hcl | qs pH 7 |
| Demineralized water | qs 100 |

3 - Aqueous stick:

A deodorant aqueous stick of the composition below was prepared:

| | |
|---|---|
| Sodium stearate | 6.2% |
| Glycerol | 15% |
| Propylene glycol | 20% |
| STARBURST PAMAM DENDRIMER of generation 1 | 1.8% |
| Fragrance | qs |
| Demineralized water | qs 100 |

4 - Deodorant cream:

A deodorant cream was prepared in the form of an oil-in-water emulsion of the following composition:

| | |
|---|---|
| Oily phase: | |
| Mixture of cetylstearyl alcohol and oxyethylenated cetylstearyl alcohol (33 EO) sold under the name DEHSCONET 390 by the company Tensia | 7% |
| (Mono- and di-)glyceryl stearate sold under the name GELEOL COPEAUX by the company Gattefosse | 2% |
| Cetyl alcohol | 11.5% |
| Polydimethylsiloxane sold under the name SILBIONE OIL 70 047 V300 by the company Rhône Poulenc | 1.5% |
| Liquid petroleum jelly | 15% |
| Glycerol | 20% |
| Aqueous phase: | |
| STARBURST PAMAM DENDRIMER of generation 1 | 1.8% |
| Propylene glycol | 20% |
| Fragrance | qs |
| Preserving agents | qs |
| Hcl | qs pH 7 |
| Demineralized water | qs 100 |

This cream was effective at inhibiting the development of human underarm odors.

We claim:

1. A deodorant composition comprising at least one dendrimer containing at least one terminal group bearing a primary amine function.

2. A deodorant composition according to claim 1, wherein said at least one dendrimer is a polyamidoamine or a polyalkylamine.

3. A deodorant composition according to claim 2, wherein said at least one dendrimer is selected from 1st generation polyamidoamines, 2nd generation polyamidoamines, 3rd generation polyamidoamines, 4th generation polyamidoamines, and 5th generation polyamidoamines.

4. A deodorant composition according to claim 3, wherein said at least one dendrimer is a 1st generation polyamidoamine.

5. A deodorant composition according to claim 1, wherein the primary amine function of said at least one dendrimer is neutralized.

6. A deodorant composition according to claim 1, wherein said at least one dendrimer is present in a concentration ranging from 0.01 to 10% by weight relative to the total weight of the deodorant composition.

7. A deodorant composition according to claim 6, wherein said at least one dendrimer is present in a concentration ranging from 0.1 to 5% by weight relative to the total weight of the deodorant composition.

8. A deodorant composition according to claim 7, wherein said at least one dendrimer is present in a concentration ranging from 0.1 to 2% by weight relative to the total weight of the deodorant composition.

9. A deodorant composition according to claim 1, wherein said deodorant composition further comprises an additional deodorant active agent.

10. A deodorant composition according to claim 1, wherein said deodorant composition is formulated in an essentially aqueous vehicle.

11. A deodorant composition according to claim 1, wherein said deodorant composition is formulated as a water-in-oil emulsion, an oil-in-water emulsion or a water-in-oil-in-water triple emulsion.

12. A deodorant composition according to claim 1, wherein said deodorant composition is in the form of a fluid gel, cream or lotion distributed as an aerosol spray, in a pump-dispenser bottle or as a roll-on; in the form of a thick cream distributed in a tube; or in the form of a stick.

13. A method for inhibiting the development of odors, said method comprising:
including a deodorant composition according to claim 1 as a deodorant active agent in a cosmetic product, and
applying said cosmetic product topically on human skin.

14. A method for inhibiting the development of odors, said method comprising including a deodorant composition according to claim 1 as a deodorant active agent in an odor-inhibiting product.

15. A method for treating human underarm odors, said method comprising applying an effective amount of a deodorant composition according to claim 1 to the underarm area.

16. A deodorant composition according to claim 10, wherein said deodorant composition further contains a $C_1$–$C_4$ monoalcohol.

* * * * *